United States Patent [19]

Hill et al.

[11] Patent Number: 4,554,369

[45] Date of Patent: Nov. 19, 1985

[54] ORGANOSILICON COMPOUNDS AND PREPARATION AND USE THEREOF

[75] Inventors: Michael P. Hill, Saint Lythans, Wales; Gilbert H. Pittet, Coppet, Switzerland

[73] Assignee: Dow Corning Ltd., Barry, Wales

[21] Appl. No.: 641,523

[22] Filed: Aug. 16, 1984

[51] Int. Cl.[4] .......................... C07F 7/08; C07F 7/10; C07F 7/18

[52] U.S. Cl. .................................. 556/418; 556/440; 424/59

[58] Field of Search .................... 556/440, 418; 424/59

[56] References Cited

U.S. PATENT DOCUMENTS

| | | | |
|---|---|---|---|
| 3,068,152 | 12/1962 | Black | 167/90 |
| 3,068,153 | 12/1962 | Morehouse | 167/90 |
| 3,513,184 | 5/1970 | Brison et al. | 556/418 |
| 3,853,935 | 12/1974 | Roshby et al. | 556/418 |
| 4,472,590 | 9/1984 | Mitchell | 556/418 |

FOREIGN PATENT DOCUMENTS

| | | | |
|---|---|---|---|
| 2215629 | 10/1973 | Fed. Rep. of Germany | 556/418 |
| 1164522 | 9/1969 | United Kingdom | |
| 1373458 | 11/1974 | United Kingdom | |
| 2030581 | 4/1980 | United Kingdom | 556/440 |

*Primary Examiner*—Paul F. Shaver
*Attorney, Agent, or Firm*—George A. Grindahl

[57] ABSTRACT

Organosilicon compounds which are silanes or siloxanes characterized by the presence of silicon-bonded groups represented by the general formula

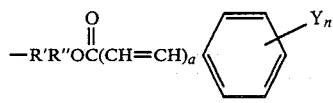

in which R' is a divalent hydrocarbon group which may contain ether oxygen, R" represents —CHBCH$_2$— or —C$_6$H$_9$B— in which B is OH or the group

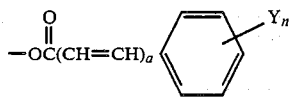

a and n are each 0 or 1 and Y is —OH, lower alkoxy or —NX$_2$ wherein X represents hydrogen or lower alkyl.

The compounds are prepared by the reaction of an organosilicon compound having an organic substituent which contains an epoxy group, and the appropriate acid or acid chloride. They absorb ultra violet radiation and are useful as cosmetic and other sunscreen agents.

9 Claims, No Drawings

ORGANOSILICON COMPOUNDS AND PREPARATION AND USE THEREOF

This invention relates to novel organosilicon compounds having U.V. absorbing properties and which are useful inter alia as sunscreen agents.

A number of organic compounds, generally organic acids and their derivatives, are known to have U.V. absorbing properties and are employed on a commercial scale as effective ingredients in sunscreen preparations. Although such materials function adequately they are easily removed from the substrate to which they have been applied. For example cosmetic sunscreen preparations are at least partially removed during bathing thus requiring repeated applications if protection is to be maintained. It is also desirable that the active ingredients remain on the skin rather than being absorbed thereby.

U.S. Pat. Nos. 3,068,152 and 3,068,153 disclose sunburn preventive compositions comprising an inert, non-toxic, non U.V.-light absorbing carrier having dispersed therein respectively an organosilicon compound containing at least one silicon-bonded phenylcarbamylalkyl group or at least one silicon-bonded acylaminoalkyl group. The presence of relatively large proportions of such groups in the molecule, however, appears to lead to siloxane products of high viscosity and even to solid products. Such products are generally less desirable for cosmetic applications than are the oily less viscous siloxanes.

British Pat. No. 1,164,522 discloses organosilicon compounds which are useful as sunscreen agents and which may be prepared by the reaction of allyl cinnamate with an organosiloxane having silicon-bonded hydrogen atoms in the molecule. Due to the occurrence of secondary rearrangement reactions the yield of desired product is generally poor. A method of preparing organosilicon cinnamates which avoids such secondary reactions is described in British Pat. No. 1,373,458. The said method involves the reaction of allyl cinnamate with a silane or siloxane containing mercaptoalkyl, e.g. 3-mercaptopropyl groups. Usually, however, some residual odour of the mercaptoalkyl starting materials remains in the product thus rendering it unsuitable for cosmetic applications.

According to this invention there are provided organosilicon compounds which are (1) silanes represented by the general formula

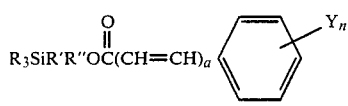

or (2) organosiloxanes having at least one unit represented by the general formula

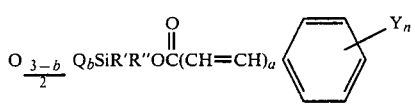

any other units present in the said organosiloxanes being those represented by the general formula

wherein each R represents an alkoxy group or an alkoxyalkoxy group having less than 8 carbon atoms, an alkyl group having from 1 to 4 inclusive carbon atoms, a vinyl group or a phenyl group, R' represents a divalent hydrocarbon group composed of carbon, hydrogen and, optionally, oxygen present in the form of ether linkages, R" represents the group

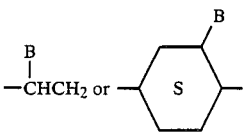

in which B represents —OH or, except when Y is —OH or $NH_2$, is Cl or the group

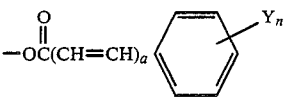

a and n are each 0 or 1, Y when present being —OH or an alkoxy group having from 1 to 4 carbon atoms when a is 1 and —OH or —$NX_2$, wherein X represents hydrogen or an alkyl group having from 1 to 4 carbon atoms, when a is zero, Q represents a hydroxyl group, an alkoxy or alkoxyalkoxy group having less than 8 carbon atoms, a methyl group or a phenyl group, Z represents a hydrogen atom, a monovalent hydrocarbon group or a monovalent halogenated hydrocarbon group, b is 0, 1 or 2 and c is 0, 1, 2 or 3.

In the general formula of the silanes each R may be for example methoxy, ethoxy, isopropoxy, methoxyethoxy, ethoxyethoxy, methyl, ethyl, vinyl or phenyl. The divalent group R' may be for example —$(CH_2)_3$—, —$(CH_2)_4$—, —$CH_2.CHCH_3CH_2$—, —$(CH_2)_3OCH_2$— or —$CH_2.CHCH_3CH_2OCH_2$—. When a is unity the substituent Y, if present (n=1), represents the hydroxy or a lower alkoxy e.g. methoxy group. When a is zero the substituent Y may represent a hydroxyl group or the amino group —$NX_2$ wherein each X may represent e.g. methyl, ethyl or n-propyl.

Examples of the silanes of this invention therefore are

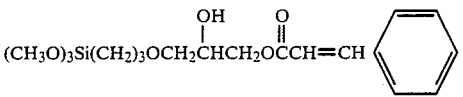

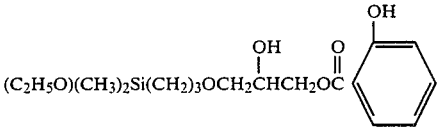

and

-continued

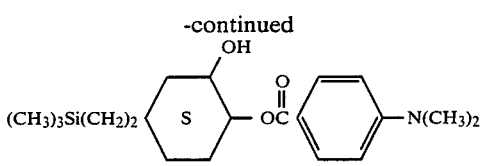

The siloxanes of this invention have in the molecule at least one unit falling within the general formula (i). They may be homopolymers consisting of only such units (i) or they may be copolymers containing both units (i) and units falling within the general formula (ii). In the general formulae defining the siloxane homopolymers and copolymers of this invention R', R", Y, a and n are as specified and exemplified hereinabove. Each of the substituents Q may be —OH, methyl, phenyl or an alkoxy or alkoxyalkoxy group e.g. methoxy, ethoxy, isopropoxy, methoxyethoxy or ethoxyethoxy. Each of the Z substituents may be hydrogen or a monovalent hydrocarbon or halogenated hydrocarbon group, preferably having less than 8 carbon atoms. Each Z may therefore be, for example, H, methyl, propyl, vinyl, phenyl or 3,3,3-trifluoropropyl.

The siloxanes of this invention may vary in molecular size from the disiloxanes to high molecular weight homopolymers and copolymers and may range in consistency from freely flowing liquids to resinous solids. Preferred, at least for cosmetic applications are the oily, liquid, substantially linear siloxane homopolymers and copolymers. It is also preferred for such applications that at least 30 percent and preferably at least 70 percent of the Q and Z substituents be methyl groups.

It has been found that compounds wherein Y represents lower alkoxy e.g. methoxy or —NX$_2$ e.g. dimethylamino exhibit high absorbance in the erythemic region (290–320 nm). Such compounds are therefore preferred for use in applications e.g. cosmetic sunscreen products where absorbtion in this region of the U.V. spectrum is desired.

The siloxanes of this invention may be prepared by reacting a siloxane having at least one silicon-bonded substituent containing an epoxy group

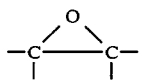

with the appropriate organic acid or acid chloride. The silanes of this invention may be prepared by a similar route. This invention therefore also provides a process for the preparation of an organosilicon compound which comprises reacting together (A) a compound of the general formula

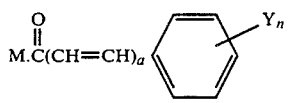

and (B) an organosilicon compound which is a silane of the general formula $R_3SiR'X$ or a siloxane having in the molecule at least one unit of the general formula

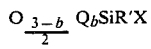

any other units present in the organosiloxane being those represented by the general formula

wherein, in the general formulae X represents the group

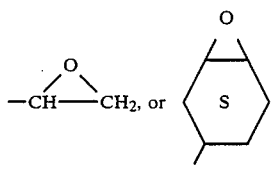

and each M represents Cl or OH and R, R', Q, Y, Z, b, c and n are as hereinabove defined.

Reactant (A) employed in the process of this invention is an aromatic organic acid, for example, cinnamic acid, methoxycinnamic acid, hydroxybenzoic acid and p-dimethylaminobenzoic acid, or the corresponding acid chloride, for example cinnamoyl chloride. As hereinbefore indicated the preferred products are those obtained when Y is a lower alkoxy group or the —NX$_2$ group.

The epoxidised organosilicon reactants (B) are, in general, known substances and can be prepared for example by the reaction of an organosilicon compound containing at least one silicon-bonded hydrogen atom with an aliphatically unsaturated epoxy compound, for example allyl glycidyl ether, methallyl glycidyl ether or vinylcyclohexene monoepoxide. From considerations of commercial availability and economy the silanes and siloxanes derived employing allyl glycidyl ether are preferred.

The reaction between (A) and (B) is preferably carried out at elevated temperatures, generally from about 50° C. up to the reflux temperature of the reaction mixtures. Catalysts may be employed to expedite the reaction if desired. Suitable catalysts include tertiary amines, inorganic bases, alkali metal salts, and Lewis acids and bases. Also, if desired, solvents may be employed to facilitate the reaction or assist in the recovery of the reaction products. Suitable solvents include for example toluene, xylene, petroleum ether, esters, ethers and alcohols.

Preferably the reaction is performed employing stoichiometric proportions of (A) and (B) or a slight stoichiometric excess of (A).

Compounds wherein B represents the group

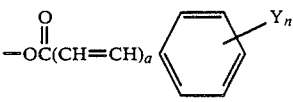

may be prepared by the reaction of the corresponding compounds wherein B is OH (Y not —OH or —NH$_2$) with an acid chloride. The said acid chloride may, if desired, be derived from a different acid from that employed to prepare the hydroxylated organosilicon compound. Thus, for example, an organosilicon compound prepared from methoxy cinnamic acid may be further reacted with cinnamoyl chloride to provide an organosilicon compound having both acid groups therein. Thus by suitable choice of the acid and acid chloride reactants organosilicon compounds having a variety of absorption spectra can be obtained.

The compounds of this invention absorb ultra-violet radiation and are therefore useful as agents for preventing sunburn. They may be applied per se to the skin but are more preferably formulated into compositions with, for example, inert carriers e.g. solvents such as ethanol, isopropanol, glycerine and mineral oil, and cream base materials such as stearic acid, propylene glycol, beeswax and cetyl alcohol. Other conventional ingredients e.g. perfumes and known U.V. absorbing substances may also be included in the formulated compositions. The organosilicon compounds of this invention are also useful in the coating of substrates e.g. wood, plastics or metal, either per se or as additives to coating compositions.

The following examples in which the parts are expressed by weight and Me=methyl, illustrate the invention.

EXAMPLE 1

49 g (0.275 mole) of p-methoxycinnamic acid, 62.7 g of the siloxane

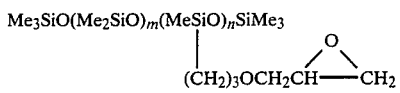

wherein m=3 and n=5, and 146 g of toluene were charged to a 500 ml flask fitted with a condenser and thermometer. A nitrogen blanket was introduced over the surface of the reaction mixture which was then heated to 110° C. N,N-dimethylethanolamine (0.8 g) in toluene (4 g) was added to the flask and the reaction mixture maintained at 105°–115° C. for 4½ hours. The reaction mixture was then allowed to cool to 60° C. and the excess p-methoxycinnamic acid removed by filtration.

The filtrate was stripped of volatiles to 130° C. and 50 mm.Hg to yield 85 g of a viscous, pale brown liquid polymer having the structure

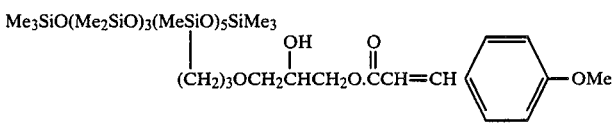

The polymer had a molar extinction coefficient of 20,000 per cinnamate (λ max 308 nm). The extinction coefficient of a 1% solution in methylene chloride was 437.

EXAMPLE 2

Employing the procedure described in Example 1 and a siloxane wherein m=95 and n=5 the following polymer was prepared:

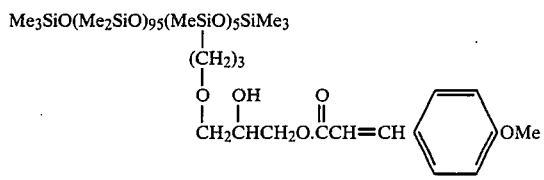

The polymer had a molar extinction coefficient (λ max 308 nm) of 13,000 per cinnamate. The extinction coefficient for a 1% solution in methylene chloride was 73.

EXAMPLE 3

The general procedure described in Example 1 was employed to react p-methoxycinnamic acid and a polydimethylsiloxane having an epoxy-substituted organic group attached to each terminal silicon atom, using anhydrous potassium acetate as catalyst. The following polymer was obtained

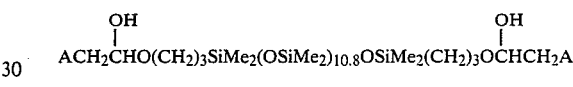

wherein A represents the group

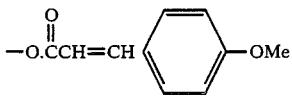

50 g of this polymer and 10 g of toluene were placed in a flask and 15 g of cinnamoyl chloride dissolved in 10 g of toluene slowly added to the flask at room temperature. The reaction mixture was then heated to 100° C. and held at that temperature for 1 hour. On cooling triethylamine (9.6 g) was added to neutralise HCl, the resulting mixture was filtered and the filtrate stripped of volatiles to 179° C. at 50 mm.Hg.

The product was an oily liquid of viscosity 360 cS at 25° C. having the structure

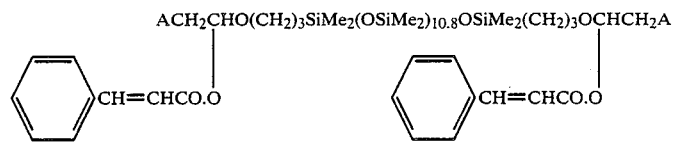

EXAMPLE 4

31.1 g of salicylic acid, 2.54 g of anhydrous sodium acetate, 40 g of amyl acetate and 100 g of the siloxane

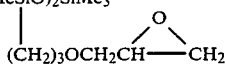

were charged to a flask fitted with condenser, agitator and nitrogen purge. The mixture was heated to 140° C. and held at this temperature for 19 hours. After cooling the mixture was filtered, heated under vacuum to remove volatile materials and filtered again. The resulting product was a siloxane polymer, of orange colour and having the following properties
Viscosity (15° C.): 610 cP
λ max: 307 nm
Molar extinction coefficient: 4623

EXAMPLE 5

28.5 g of the epoxy siloxane reactant described in Example 4, 7.64 g of p-aminobenzoic acid, 0.07 g N,N-dimethylethanolamine and 35 g of amyl acetate were charged to a flask fitted as described in Example 4 and the mixture heated at 100°-129° C. for 6.5 hours. After filtration and removal of volatiles a viscous orange-coloured siloxane polymer was obtained having λ max=292.6. The polymer was soluble in dichloromethane.

EXAMPLE 6

100 g of the epoxy-substituted siloxane reactant employed in Example 4, 31.1 g of p-N,N-dimethylaminobenzoic acid, 0.27 g of N,N-dimethylethanolamine and 39.3 g amyl acetate were charged to a flask and reacted at 150° C. for 7.5 hours. After filtration and removal of volatiles a yellow liquid was obtained having the following properties
Viscosity (25° C.): 2000 cP
λ max: 313 nm
Molar extinction coefficient: 26730

EXAMPLE 7

177 g of a siloxane having the average structure

wherein A=

44.3 g p-methoxycinnamic acid, 4.3 g anhydrous potassium acetate and 53.9 g amyl acetate were heated together at 140° C. under a nitrogen purge for 6 hours. After filtration and removal of volatile materials a pale yellow liquid was obtained having the following properties
Viscosity (25° C.): 124 cP
λ max: 310 nm
Extinction coefficient (1% in $CH_2Cl_2$) 127 An oil-in-water emulsion was prepared by mixing this siloxane product (3 g), polydimethylsiloxane (50 cP viscosity) (2 g), cetyl alcohol (2 g) and Polawax cP 200 (4 g). The mixture was heated to 70° C. and added to water (89 g) also at 70° C. with stirring. A thin creamy emulsion was obtained which became more viscous on further homogenisation employing a Silverson mixer.

EXAMPLE 8

A siloxane water-in-oil emulsion was prepared by adding 73 g of water and 2 g of sodium chloride to an oil phase consisting of

| | |
|---|---|
| Siloxane product of Example 7 | 4 g |
| Ethoxylated secondary alcohols (Tergitol 15 S3) | 0.5 g |
| Cyclomethicone | 11.0 g |
| Cyclomethicone/dimethicone copolyol | 9.5 g |

The emulsion was a thin cream useful as a skin lotion. After further homogenisation employing a mechanical mixer (Silverson) a thick cream was obtained.

That which is claimed is:
1. Organosilicon compounds which are
(1) silanes represented by the general formula

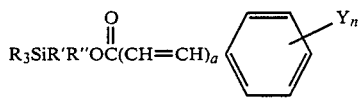

or (2) organosiloxanes having at least one unit represented by the general formula

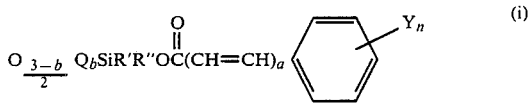 (i)

any other units present in the said organosiloxanes being those represented by the general formula $$Z_c SiO_{\frac{4-c}{2}}$$ (ii)

wherein each R represents an alkoxy group or an alkoxyalkoxy group having less than 8 carbon atoms, an alkyl group having from 1 to 4 inclusive carbon atoms, a vinyl group or a phenyl group, R' represents a divalent hydrocarbon group composed of carbon, hydrogen and, optionally, oxygen present in the form of ether linkages, R" represents the group

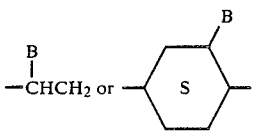

in which B represents —OH or, except when Y is —OH or $NH_2$, is Cl or the group

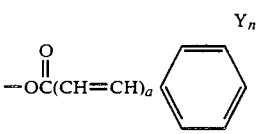

a and n are each 0 or 1, Y when present being —OH or an alkoxy group having from 1 to 4 carbon atoms when a is 1 and —OH or $NX_2$, wherein X represents hydrogen or an alkyl group having from 1 to 4 carbon atoms, when a is zero, Q represents a hydroxyl group, an alkoxy or alkoxyalkoxy group having less than 8 carbon atoms, a methyl group or a phenyl group, Z represents a hydrogen atom, a monovalent hydrocarbon group or a monovalent halogenated hydrocarbon group, b is 0, 1 or 2 and c is 0, 1 or 3.

2. Organosilicon compounds as claimed in claim 1 wherein a is 1 and Y represents a lower alkoxy group.

3. Organosilicon compounds as claimed in claim 1 wherein a is 0 and Y represents the —NX$_2$ group.

4. Organosiloxanes as claimed in claim 1 wherein at least 70 percent of the total Q and Z substituents are methyl groups.

5. A process for the preparation of organosilicon compounds as defined in claim 1 which comprises reacting together (A) a compound of the general formula

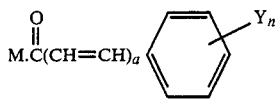

and (B) an organosilicon compound which is a silane of the general formula

R$_3$SiR'X or a siloxane having in the molecule at least one unit of the general formula

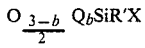

any other units present in the organosiloxane being those represented by the general formula

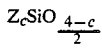

wherein, in the general formulae X represents the group

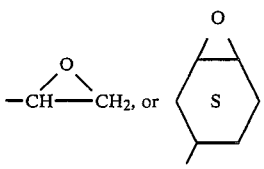

and each M represents Cl or OH and R, R', Q, Y, Z, b, c and n are as hereinabove defined.

6. A process as claimed in claim 5 wherein Y represents an alkoxy group having from 1 to 4 inclusive carbon atoms.

7. A process as claimed in claim 5 wherein Y represents the group —NX$_2$ in which X represents an alkyl goup having from 1 to 4 carbon atoms.

8. A process as claimed in claim 5 wherein B in the product represents a hydroxyl group and the product is further reacted with an acid chloride.

9. A sunscreen composition which contains a carrier and an effective amount of an organosilicon compound as claimed in claim 1.

* * * * *

UNITED STATES PATENT AND TRADEMARK OFFICE
CERTIFICATE OF CORRECTION

PATENT NO. : 4,554,369

DATED : November 19, 1985

INVENTOR(S) : Michael P. Hill and Gilbert H. Pittet

It is certified that error appears in the above-identified patent and that said Letters Patent is hereby corrected as shown below:

The following should be added to the cover page of the patent:

-- Foreign Application Priority Data
   August 18, 1983   Great Britain   8322317 --.

Signed and Sealed this

Twenty-sixth Day of August 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,554,369

DATED : November 19, 1985

INVENTOR(S) : Michael P. Hill and Gilbert H. Pittet

It is certified that error appears in the above-identified patent and that said Letters Patent is hereby corrected as shown below:

In Col. 8, line 60, " 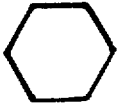 " should read

--  --.

Signed and Sealed this

Twenty-fifth Day of November, 1986

Attest:

DONALD J. QUIGG

Attesting Officer     Commissioner of Patents and Trademarks